United States Patent [19]
Tankovich et al.

[11] Patent Number: 5,817,089
[45] Date of Patent: *Oct. 6, 1998

[54] SKIN TREATMENT PROCESS USING LASER

[75] Inventors: Nikolai I. Tankovich, San Diego; Lawrence H. Sverdrup, Jr., Poway; Richard G. Episcopo, San Diego, all of Calif.

[73] Assignee: ThermoLase Corporation, San Diego, Calif.

[ * ] Notice: The term of this patent shall not extend beyond the expiration date of Pat. No. 5,423,803.

[21] Appl. No.: 489,358

[22] Filed: Jun. 12, 1995

Related U.S. Application Data

[63] Continuation-in-part of Ser. No. 280,928, Jul. 26, 1994, abandoned, Ser. No. 257,021, Jun. 8, 1994, Pat. No. 5,423,803, and Ser. No. 5,810, Jan. 19, 1993, Pat. No. 5,425,728, which is a continuation-in-part of Ser. No. 783,789, Oct. 29, 1991, Pat. No. 5,226,907.

[51] Int. Cl.⁶ ..................................................... A61B 17/36
[52] U.S. Cl. .................................. 606/9; 606/2; 128/898
[58] Field of Search .................................. 606/9–19, 131, 606/133; 128/898; 607/88–90

[56] References Cited

U.S. PATENT DOCUMENTS

| | | |
|---|---|---|
| 3,538,919 | 11/1970 | Mayer . |
| 3,693,623 | 9/1972 | Harte et al. . |
| 3,769,963 | 11/1973 | Goldman et al. . |
| 3,794,028 | 2/1974 | Mueller et al. . |
| 3,834,391 | 9/1974 | Block . |
| 3,900,034 | 8/1975 | Katz et al. . |
| 4,336,809 | 6/1982 | Clark . |
| 4,388,924 | 6/1983 | Weissman et al. . |
| 4,461,294 | 7/1984 | Baron . |
| 4,608,978 | 9/1986 | Rohr . |
| 4,617,926 | 10/1986 | Sutton . |
| 4,712,543 | 12/1987 | Baron . |

(List continued on next page.)

FOREIGN PATENT DOCUMENTS

| | | |
|---|---|---|
| 1041610 | 6/1974 | Canada . |
| 1208702 | 7/1986 | Canada . |
| D64967A2 | 4/1995 | European Pat. Off. . |
| 2267122 | 4/1975 | France . |
| 2595239 | 6/1982 | France . |
| 2590791 | 6/1987 | France . |

(List continued on next page.)

OTHER PUBLICATIONS

Porphyrins in Tumor Phototherapy—Andereoni 1984—pp. 143–155.

Investigation and Therapy in Dermatology A. Anders, et al—Conf. Laser 77 Optics—Electronics (20–24 Jun. 1977).

*Primary Examiner*—Glenn K. Dawson
*Attorney, Agent, or Firm*—Fish & Richardson P.C.

[57] ABSTRACT

The present invention provides a very simple easily administered skin treatment process for (1) the removal of superficial epidermal skin cells in the human skin (2) the reduction or removal of unwanted hair and (3) the mitigation of skin conditions such as acne and seborrhea. A contaminant having a high absorption at at least one wavelength of light is topically applied to a section of the surface of the skin. A preferred contaminant is a mixture of 20% by weight of one micron graphite particles in mineral oil. Graphite is a very strong absorber of 1.06 micron light produced by the Nd:YAG laser. Portions of the contaminant are forced to infiltrate into spaces between the superficial epidermal cells, into hair ducts in the skin and into and/or adjacent to sebaceous glands. The skin section is illuminated with short laser pulses at the matching wavelength, so as to impact sufficient energy to the contaminant to cause explosion in the contaminant. The energy released in the course of the explosions may blow off layers of dead skin cells and/or destroy tissue responsible for hair growth and/or sebum production.

32 Claims, 8 Drawing Sheets

U.S. PATENT DOCUMENTS

| | | |
|---|---|---|
| 4,813,412 | 3/1989 | Yamazaki . |
| 5,059,192 | 10/1991 | Zaias . |
| 5,473,803 | 12/1995 | Tankovich et al. ............ 606/131 |

FOREIGN PATENT DOCUMENTS

| | | |
|---|---|---|
| 2515697 | of 0000 | Germany . |
| 32209G2 | 6/1982 | Germany . |
| 63-249577 | 10/1988 | Japan . |
| 8002640 | 12/1980 | WIPO . |
| 8602783 | 5/1986 | WIPO . |
| WO90/11797 | 10/1990 | WIPO . |
| 9104073 | 4/1991 | WIPO . |
| WO91/13652 | 9/1991 | WIPO . |
| WO91/13653 | 9/1991 | WIPO . |
| WO93/21842 | 11/1993 | WIPO . |
| WO93/21992 | 11/1993 | WIPO . |

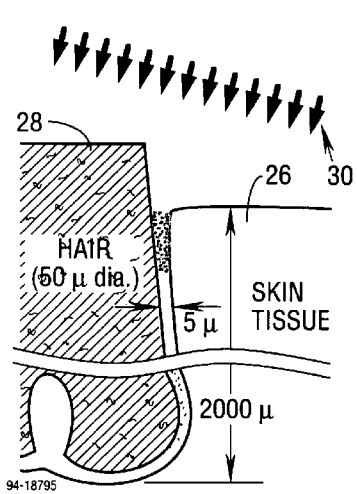
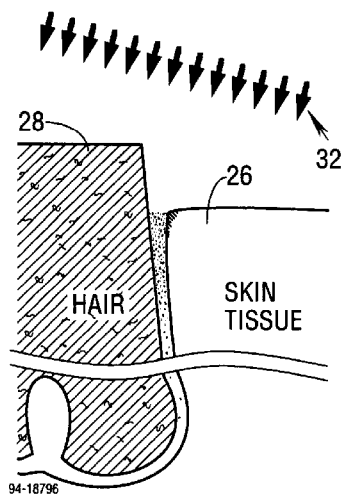
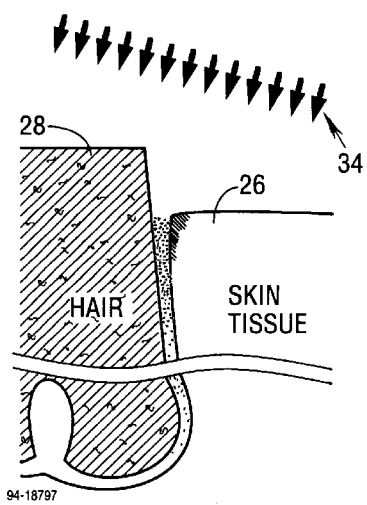
FIG. 4A  FIG. 4B  FIG. 4C
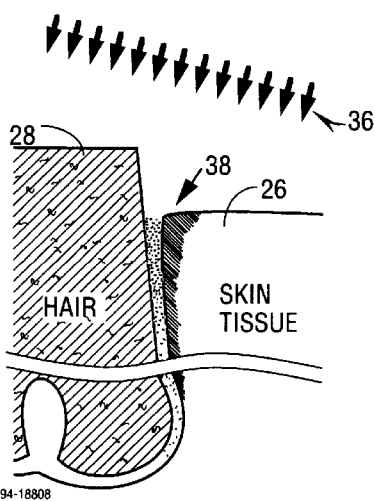
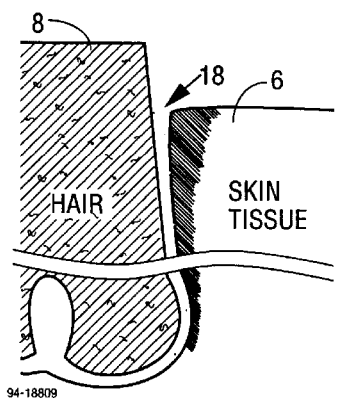
FIG. 4D  FIG. 4E

SKIN TREATMENT PROCESS USING LASER

This invention is a continuation in part of Ser. No. 08/280,928 filed Jul. 16, 1994, now abandoned, Ser. No. 08/257,021 filed Jun. 8, 1994 now U.S. Pat. No. 5,423,803, and Ser. No. 08/005,810 filed Jan. 19, 1993, now U.S. Pat. No. 5,425,728 which was a continuation in part of Ser. No. 07/783,789 filed Oct. 29, 1991, now U.S. Pat. No. 5,226,907 issued Jul. 13, 1993. This invention relates to processes for skin treatment and in particular to such processes which utilize lasers.

BACKGROUND OF THE INVENTION

The Skin

A section of human skin showing a cross section of one hair is shown in FIG. 1. FIG. 1 shows the hair shaft 33 of a hair growing in a hair duct 31, from dermal papilla 32, a nerve ending 34, a sweat gland 35 a sebaceous gland 38, arteries 36 and veins 37.

Three major concerns relating to human skin are (1) accumulation of excess layers of dead skin cells on middle age and elderly people which cause them to appear older, (2) skin conditions such as acne and seborrhea and (3) unwanted hair.

Dead Layers of Skin

The epidermis, 39 in FIG. 1, of the human skin comprises several distinct layers of skin tissue. These layers of tissue are depicted in block diagram form in FIG. 2. The deepest layer is the stratum basale layer which consists of columnar cells. The next layer up is the stratum spinosum composed of polyhedral cells. Cells pushed up from the stratum spinosum are flattened and synthesize keratohyalin granules to form the stratum granulosum layer. As these cells move outward they lose their nuclei and the keratohyalin granules fuse and mingle with tonofibrils. This forms a clear layer called the stratum lucidum. The cells of the stratum lucidum are closely packed. As the cells move up from the stratum lucidum they become compressed into many layers of opaque squamas. These flattened cells have become completely filled with keratin and have lost all other internal structure, including nuclei. These squamas constitute the outer layer of the epidermis, the stratum corneum. At the bottom of the stratum corneum the cells are closely compacted and adhere to one another strongly, but higher in the stratum they become loosely packed and eventually flake away at the surface. For example, in the cheek skin of a 50 year old face the outer layer of the stratum corneum typically consists of about 15 layers, and the layers flake away at the rate of about one or two layers per month. So we naturally get a completely new stratum corneum on our faces about twice per year.

It is well known that the removal of a few surface layers of a person's skin will generally result in younger looking skin. Many techniques have been tried to produce this effect. A mild sunburn will cause slight blistering of the skin after which an outside layer of the skin peels off. This generally leaves a younger looking skin surface. Similar results can be obtained by abrasion processes such as actually scraping away the surface layer with an abrasive material such as fine sand paper.

Recent attempts have been made to utilize laser beams to "cook" the surface layer of skin. This cooking causes the skin to blister after which the surface layers can be scraped away. Also, people have been experimenting with lasers which vaporize the outside surface. These prior art processes present some beneficial results but also provide potential risk to the patient. The slight sunburn presents a risk of underlying long term damage to the skin. Abrasion processes often result in bleeding and pain and sometimes infection, scabbing, and slight scarring. Laser treatments can result in pain and undesired burning, and if not applied properly can result in bleeding and scarring.

Acne and Seborrhea

Skin conditions such as acne and seborrhea are believed to be caused or exacerbated by excessive sebum flow produced by sebaceous glands most of which are adjacent to and discharge sebum into, hair follicles. Sebum is composed of keratin, fat, and cellular debris. Sebum forms a moist, oily, acidic film that is mildly antibacterial and antifungal and may to some extent protect the skin against drying. The function of the sebum excretion in man is controversial and it may very well serve no useful function whatsoever. It is known that the bacteria which cause acne is propionibacterium acne or (P-acnes). This bacteria grows in sebum. Significant sebum flow in humans begins at puberty. This is when acne problems arise. Males castrated before puberty do not develop acne or seborrhea.

Seborrhea is any of several common skin conditions in which there is an overproduction of sebum resulting in excessive oiliness or dry scales. Seborrhea includes seborrheic dermatitis (cradle cap, dandruff), seborrhea congestivea, seborrheic blepharitis, and seborrheic keratosis

Unwanted Hair

Removal of unwanted hair is a large business in the United States. Techniques include short term removal techniques such as shaving and plucking and long term (sometimes permanent) removal techniques such as electrolysis. Attempts have been made to use laser beams for hair removal. Prior art methods for permanent or long term hair removal are generally painful and very time consuming.

Graphite Particles

It is known that graphite vaporizes at about 3,600° C. It is known that graphite is a strong absorber of infrared light and that infrared light such as the 1.06 micron laser beam produced by the Nd:YAG laser will penetrate several millimeters through human skin.

What is Needed

What is needed is a simple quick treatment process which could be used to treat all of the above skin conditions.

SUMMARY OF THE INVENTION

The present invention provides a very simple easily administered skin treatment process for (1) the removal of superficial epidermal skin cells in the human skin (2) the reduction or removal of unwanted hair and (3) the mitigation of skin conditions such as acne and seborrhea. A contaminant having a high absorption at at least one wavelength of light is topically applied to a section of the surface of the skin. A preferred contaminant is a mixture of 20% by weight of one micron graphite particles in mineral oil. Graphite is a very strong absorber of 1.06 micron light produced by the Nd:YAG laser. Portions of the contaminant are forced to infiltrate into spaces between the superficial epidermal cells, into hair ducts in the skin and into and/or adjacent to sebaceous glands. The skin section is illuminated with short laser pulses at the matching wavelength, so as to impact sufficient energy to the contaminant to cause explosion in the contaminant. The energy released in the course of the explosions may blow off layers of dead skin cells and/or destroy tissue responsible for hair growth and/or sebum production.

BRIEF DESCRIPTION OF THE DRAWINGS

FIGS. 4A–E demonstrates a hair removal.

DETAILED DESCRIPTION OF PREFERRED EMBODIMENTS

Preferred embodiments of the present invention can be described by reference to the drawings.

Nd:YAG LASER AND CARBON PARTICLES IN OIL

Skin Peeling

Outer Layers of the Epidermis

A first preferred embodiment of the present invention can be described by reference to FIGS. 3 through 3J. FIG. 3 shows a typical cross section of a section of the outer portion (the top three strata) of the human epidermis such as that in the skin of a 50 year old female's cheek. Shown is a representation of a 15-cell thick stratum corneum 1, and a 3-cell thick stratum lucidum 2, and a 3-cell thick stratum granulosum. The total thickness shown is about 100 microns (0.10 mm).

Individual cells of the stratum corneum have dimensions of about 10 to 15 microns long, about 5 microns wide and up to 2 microns thick. The cells of the upper layers are loosely stuck together. Spaces between the cells range from zero distance to about 1 or 2 microns.

Application of Carbon Solution

Figure 3A:
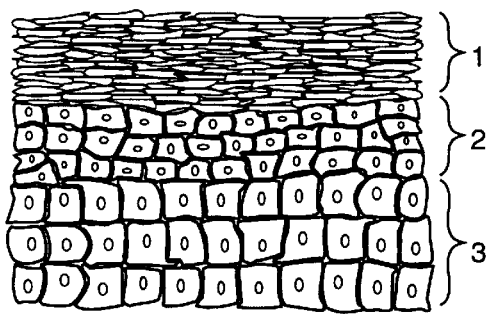
FIGS. 3A–L demonstrate skin peeling.
Figure 3B:
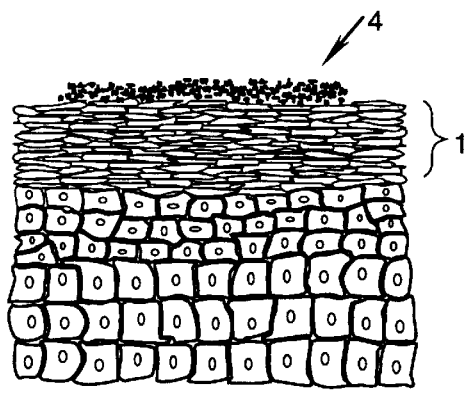
Figure 3C:
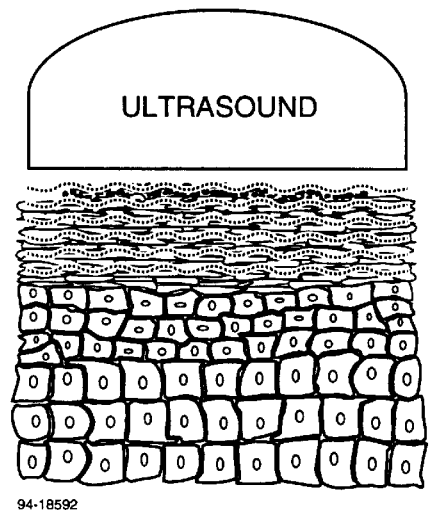

The first step of this preferred embodiment is to topically apply a layer of carbon solution to the skin surface as shown in FIG. 3B. The solution is comprised of 1 micron graphite powder in baby oil. The graphite-oil ratio is 20 percent graphite suspended in 80 percent oil by weight. The next step FIG. 3C, is to force some of the carbon particles down below the surface of the stratum corneum. We prefer to do this with an ultrasound unit operating at 0.2 watts per cm$^2$ and 10 MHz.

Figure 3D:
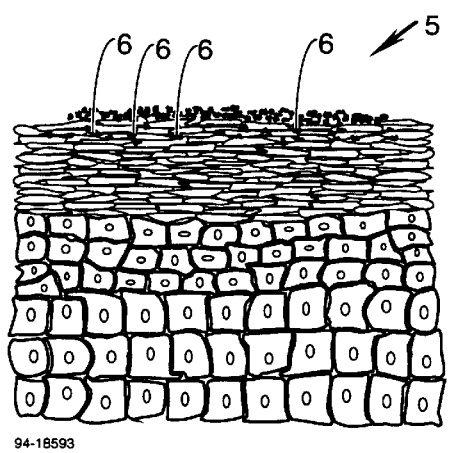

We use a Hewlett Packard Model 3325A pulse generator and a Parametrics transducer model A5525. We have found that approximately 5 minutes of ultra sound treatments at this frequency will force a significant number of carbon particles down through several layers of the stratum corneum. The result of the ultrasound treatment is shown in FIG. 3D. This distribution of carbon particles has been demonstrated on pig skin. Microscopic examination of biopsy samples from the pig skin show the distribution depicted in FIG. 3D. As shown in FIG. 3D, two layers of graphite particles are left on the surface and a portion of the particles 6 are distributed below the surface.

Pulse Irradiation

The next step is to irradiate the skin surface with Nd:YAG laser pulses of about 3 J/cm$^2$ at a wavelength of 1.06 μm. Pulse frequency is about 5 Hz but we scan the beam so that each location is subjected to pulses at a frequency of about 1 Hz. Graphite is very absorptive of laser energy at the 1.06 μm wavelength. The latent heat of vaporization is about $10^5$ J/cm$^3$ for cold solid graphite. (The energy required to heat room temperature graphite to the sublimination temperature is roughly 4% of the sublimination energy.) Thus, to vaporize a 1 micron cube ($10^{-12}$ cm$^3$) would require approximately $10^{-7}$ J. The energy falling on the surface of the 1 micron particle ($1\times10^{-8}$ cm$^2$) in a 3 J/cm$^2$ pulse is $3\times10^{-8}$ J, about one third of the energy needed to totally vaporize the particle. Therefore, a significant portion of the particle is vaporized. The energy is deposited in a few nanoseconds so there is no time for the heat to diffuse; therefore, the particle explodes violently upon being illuminated by the pulse. (Subsequent pulses will vaporize the smaller particles created by the earlier pulses.)

Figure 3E:
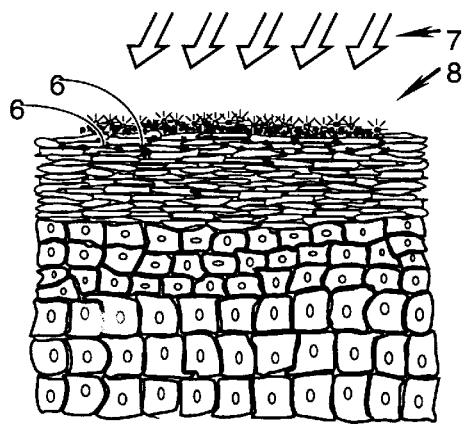
Figure 3F:
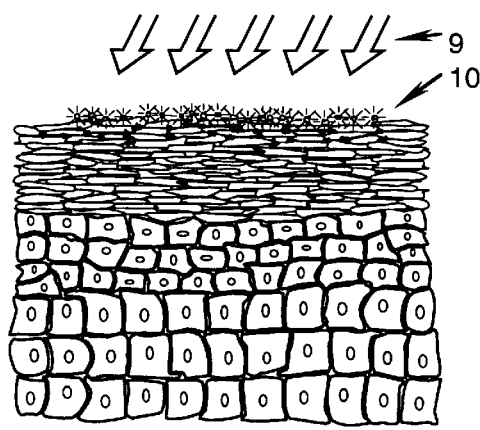
Figure 3G:
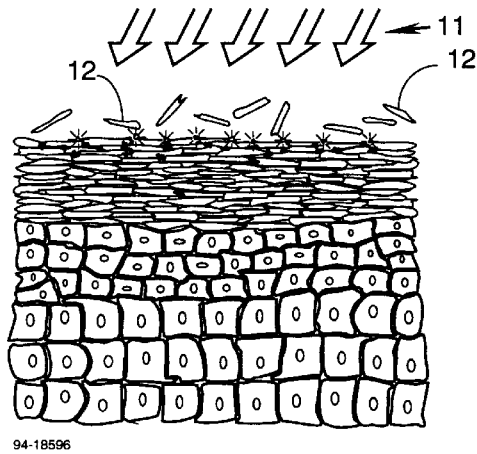
Figure 3H:
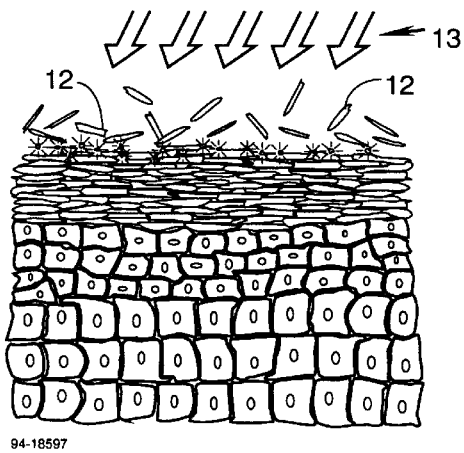
Figure 3I:
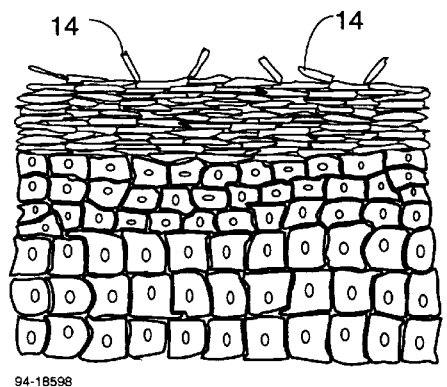

Thus, as a result of the first pulse 7 the first layer of graphite particles is exploded as shown at 8 in FIG. 3E. The second layer and the skin surface is effectively shielded from the first pulse 7 by the first layer. Some of the carbon particles above the skin have been pushed into the skin as a result of the shockwaves resulting from the explosion of the particle in the first layer. The second pulse 9 coming one second later, vaporizes the second layer as shown at 10 in FIG. 3F. As before, additional particles are pushed into the skin. The skin is fairly effectively shielded from pulse 9 by the second layer. But the third pulse 11 interacts with the skin and the carbon particle below the skin. Laser energy at a 1.06 wavelength has an extinction length in human skin of several millimeters but it is highly absorbed in the graphite particles below the surface and upon absorption of the energy from third pulse 11 as shown in FIG. 3G, the particles explode violently ripping off the dead cells of the stratum corneum which lay above the exploding cells all as shown in FIG. 3H. A few particles may be shielded from pulse 11 but three of four additional pulses 13 will assure that essentially all graphite particles are exploded as shown in FIG. 3I.

Figure 3J:
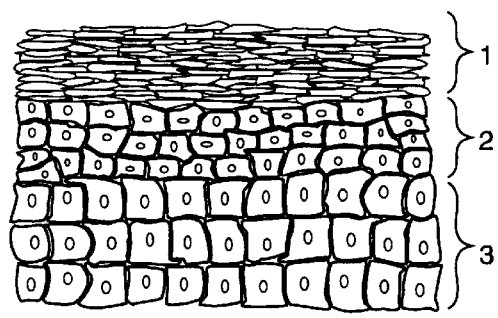

FIG. 3J shows a cross section view of the skin surface after the laser irradiation. This drawing is based on pig skin biopsy results of skin treated as described above. The skin is washed lightly with an alcohol soaked cloth and allowed to dry resulting in a surface as shown in FIG. 3J. The depiction as shown in FIG. 3J can be compared with that of FIG. 3A. We see that about three layers of the dead cells in the stratum corneum have been removed. We have observed similar effects on human skin tissue in connection with hair removal clinical experiments. For most patients, there is no pain, and no unpleasant feeling of heat. There is no significant injury to the skin tissue. The Nd:YAG laser energy which was not absorbed in the carbon is harmlessly dissipated in the skin and tissue below the skin. It is preferable to provide a slight diverging beam to assure that it spreads after it hits the skin. In our preferred embodiment the spot size at the surface is 0.5 cm (diameter) and, before interacting with the skin, is spreading at 10 degrees.

Preliminary Biopsy Studies.

Biopsy studies of both pig and human skin conducted six weeks after treatment confirm that there is no significant injury to the skin. Our preliminary conclusions from these studies indicate new collagen fiber formation in the upper part of the dermis immediately below the epidermal basal membrane. These preliminary observations indicate an abundance of fibers which are long, wavy and bound together. There appears to be an increase in the portion of young collagen fibers in the samples. We also observe what appears to be an increase in plasmocytes and young fibrocytes. These preliminary observations indicate a positive effect of the treatment in the upper layers of the dermis tissue. We have not yet developed an explanation for this indicated effect and we do not yet have sufficient experimental data to quantify the results.

Hair Removal

FIGS. 4A–4E demonstrate treatment of the skin for hair removal. In the process we use one of the same mixtures of one micron medical grade carbon (graphite) particles and mineral oil as we discuss above with respect to skin peeling. The composition is about 20% graphite by weight.

The hair in the to-be-treated section of skin is cut with a barber clipper to about a length of about 5 mm from the skin surface. The mixture is applied to the area to be treated. The mixture is massaged into the skin with a cotton swab until the hair ducts in the to-be-treated area are infiltrated to an estimated depth of about 20 microns to several millimeters. This stage of the process is depicted in FIG. 4A. In addition to the mixture infiltrated in the hair ducts, a thin film of the carbon-oil mixture (for example, about 100 particles per $cm^2$) is left on the surface of the skin in the area to be treated.

The area to be treated is then illuminated with a pulsed laser beam from a Nd:YAG laser. Preferred beam specifications are as follows:

| | |
|---|---|
| Wavelength | 1.06 micron |
| Energy per pulse | 1.5 Joules |
| Beam area | ½ $cm^2$ |
| Energy density | 3 $J/cm^2$ |
| Frequency | 10 pulses per second |

The beam is scanned over the area to be treated with each section of the skin in the area receiving about 5 pulses. The first or second pulses clean substantially all of the mixture from the skin surface by violently fracturing the carbon particles. By observing how many particles remain, the doctor can estimate the degree to which each area has been treated. As shown in FIG. 4A, the initial application of the carbon-oil mixture results in carbon particles being deposited about 20 microns deep in the duct. FIG. 4B represents the results of the first pulse 30 shown in FIG. 4A. A shockwave in the mixture spreads out the mixture for several microns. More important, the violent fragmentation of the particles sends fragments through the duct. (FIG. 4C shows qualitatively the distribution of particles after about 2 pulses.) However, with each fragmentation, the particles get smaller (FIGS. 4D and 4E) and after about 4 or 5 pulses 30 through 36 the fragments have essentially disappeared. Essentially all of the energy absorbed by the particles and fragments is transferred to the skin tissue surrounding the hair. The net result is depicted in FIG. 4E. The energy is sufficient to devitalize the tissue feeding the hair so the hair dies. In FIG. 4A through 4E arrow 38 locates the section of skin tissue damaged. Our biopsy tests indicate the thickness of the damaged sections range from zero to about 20 microns. The damage to the tissue appears to be the combined result of both the heating effect of the hot carbon particles and oil and possibly some mechanical damage due to the kinetic energy of the particles and fragments.

We have had excellent results with our human tests. In an early experiment with this improved process on my own leg essentially all hair was removed and after 24 months there has been no significant regrowth. Our clinical trials with facial hair have been on-going for 24 weeks. We have been very conservative in the application of the laser beam, but the results are very good.

No significant short term injury to the skin has been observed (only minor redness and in a very few cases some very minor bleeding). No long term injury has been observed. Hair removal success ratio in the treated area has ranged from about 0% to about 90% with the average being about 60%.

Treatment for Acne and Seborrhea

Figure 1:
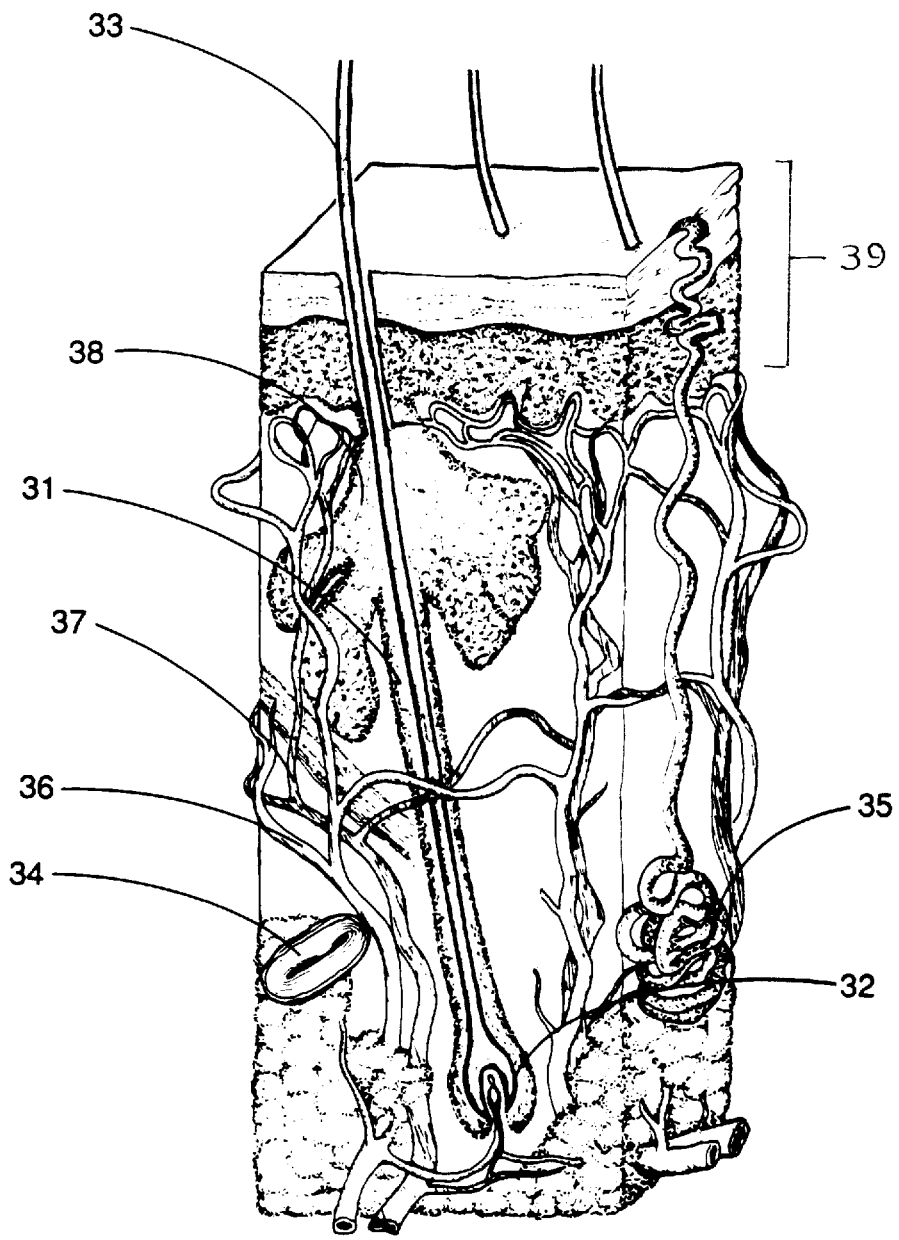
FIG. 1 shows a skin section.
Figure 2:
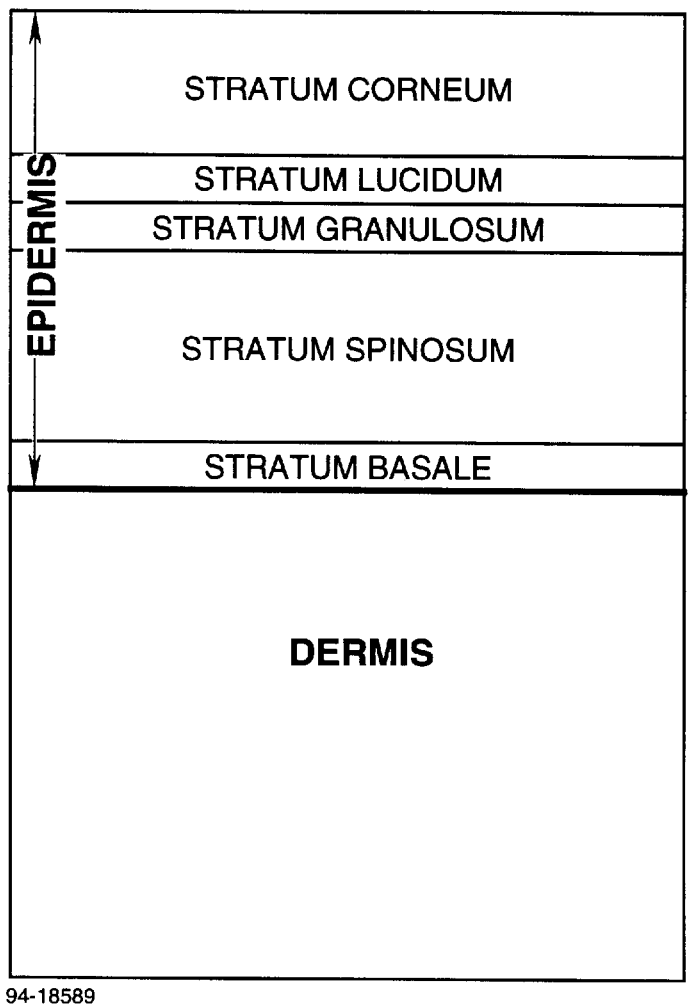
FIG. 2 is a block diagram.
Figure 5A:
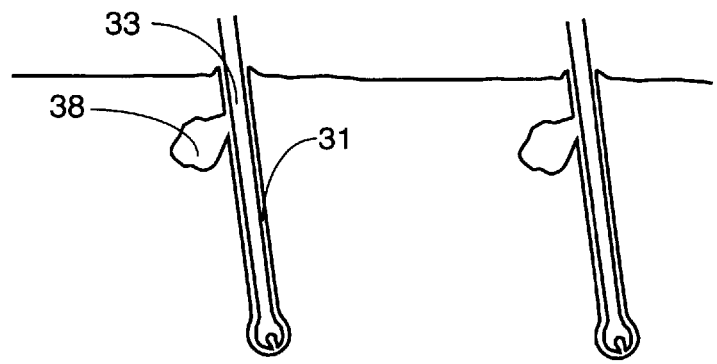
FIGS. 5A–C demonstrates an alternative hair removal and acne treatment process.

Our preferred process for treatment of acne and seborrhea is basically the same as the treatment for hair removal and skin peeling. The important difference being the section of skin treated is one in which the patient has had problems with acne or seborrhea. Preferably, the treatment is scheduled when the ducts to over active sebaceous glands are open. The carbon solution described in the preceding section is applied and caused to infiltrate into the duct leading to the sebaceous glands as shown in FIG. 5A. The portion of the sebaceous glands is also shown in FIG. 1. Laser illumination is substantially the same as for hair removal. The carbon particles within or in the vicinity of the sebaceous glands are heated to vaporization temperatures which causes the particles to fracture violently or vaporize. Energy released in the process results in full or partial destruction of epithelium tissue making up the surface of the inside wall of the sebaceous glands which tissue, produces the sebum. This results in either death or reduced effectiveness of the sebaceous glands in the section of skin treated. The consequence is a reduced sebum production. The consequence of reduced sebum production is reduced levels of acne and seborrhea.

CONFINEMENT OF PARTICLES

Figure 3K:
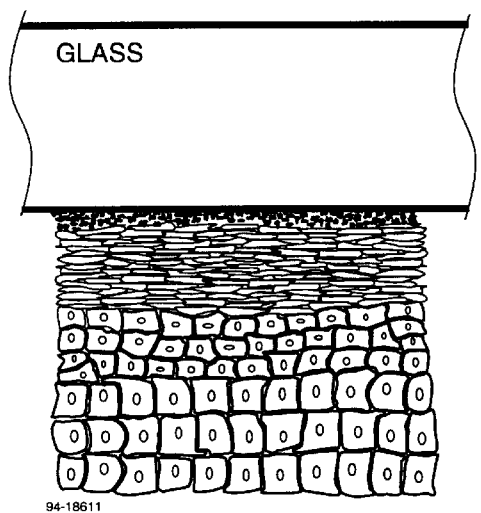
Figure 3L:
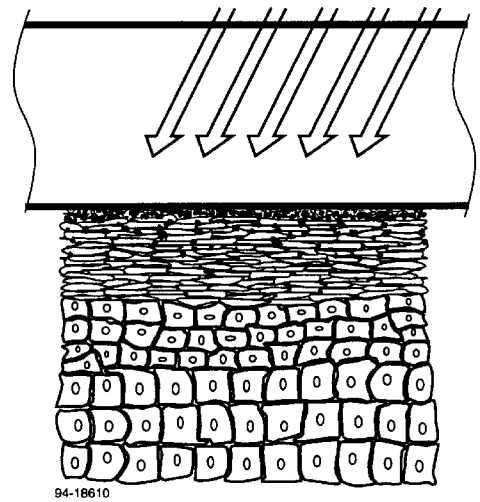

Another preferred embodiment for skin treatment is the same as the first preferred embodiment except that after the carbon-oil suspension is placed on the skin surface, a thin flat piece of glass (such as a microscope glass) is placed firmly over the suspension in order to confine the small explosions. Several pulses (preferably about 1 or 2) of the laser beam are applied through the glass onto each section of suspension. The effect is to greatly enhance the subsurface contamination of the upper layers of the epidermis with small particles of graphite. The effect is shown in FIGS. 3K and 3L. One or two pulses is sufficient to produce substantial subsurface contamination with small carbon particles. After this application the glass is removed and the process as explained above for the first embodiment is continued until essentially all of the graphite has been vaporized. In an alternate embodiment a disposable plastic plate, transparent to the laser beam could be used instead of the glass plate. The disposable plastic plate could be made a part of an articulated arm of the laser or a part of a hand piece attached to the articulated arm.

$CO_2$ LASER

A third preferred embodiment utilizes a $CO_2$ pulse laser. Preferred operating parameters are: wavelength 10.6 micron, energy density per pulse 2.5 $Joule/cm^2$, pulse diameter 1 cm, pulse duration 50 ns. Laser beams at 10.6 micron have an extinction length in skin of about 40 micron because the pulse energy is highly absorbed in water. It is much more highly absorbed in carbon. We estimate an extinction length of 1 to 2 microns.

The process is very similar to that described above. Graphite is applied as above using the ultrasound to force some of the carbon below the surface. The laser pulses are applied as above and to the first two pulses produce similar results cleaning off the two layers of carbon. The third pulse however will in addition to vaporizing carbon below the skin surface will vaporize a thin surface of tissue. Therefore, we get the combined effect of (1) mechanical removal of tissues due to the explosion of particles below the surface and (2) vaporization of a surface layer of epidermal tissue about 2–3 microns thick.

LIQUID CONTAMINANT

Instead of the carbon oil mixture discussed above, we could use other liquids or suspensions such as India ink. India ink is comprised of very small submicron graphite particles suspended in a liquid such as a water solution of alcohol. We may also use a solution of warm water colored with black food coloring at one part color per fifty parts water. Apply to skin surface with gauze for 10 minutes. The contaminant will infiltrate into the space in the upper layers of the corneum stratum. (These spaces are normally filled with air.) Remove gauze and illuminate with about 1 or 2 pulses per site using a $CO_2$ laser operating at 10.6 microns and 50 nanosecond duration pulses with an energy density of 2 Joules per $cm^2$. These short pulses will deposit sufficient energy selectively to the contaminant solution to vaporize instantly the contaminant tearing off the upper most corneum stratum cells in the skin section.

An alternative to this embodiment is to add indocyanine green to the warm water instead of the black food coloring. Indocyanine green absorbs infrared light such as that produced by the Nd:YAG, $CO_2$, Alexandrite, Ti: Sapphire and Ga:As diode lasers. Since water is an excellent absorber of $CO_2$ laser energy, many water based skin lotions could be used with the $CO_2$ laser.

REMOVAL OF HAIR (PARTIALLY OR FULLY) FROM DUCT

Figure 5B:
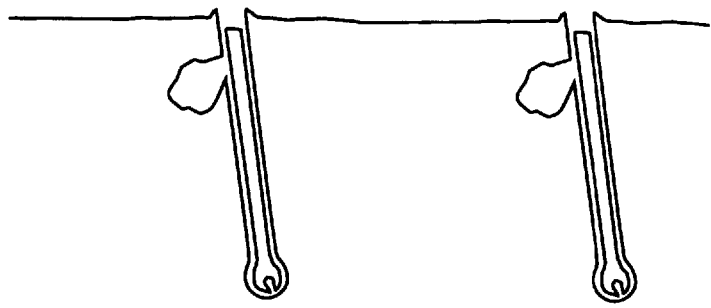
Figure 5C:
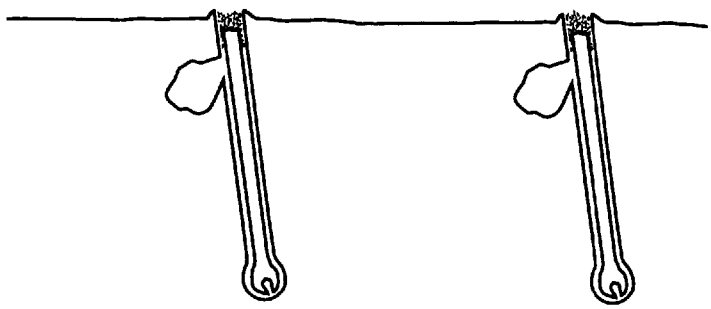

A preferred embodiment of this invention for hair removal and for acne treatment is shown in FIGS. 5 A, B and C and 6. FIG. 5A depicts 2 hairs on a skin section showing hair stem 33, hair duct 31 and the sebaceous gland 38. As shown in FIG. 5B the hair is partially removed from the hair duct below the skin surface by chemical depilation. The carbon solution is then applied to the skin section and rubbed into the skin. In this case, since the upper part of the 50 micron diameter hair is gone, there is much more room in the duct for the solution with 1 micron particles as shown in FIG. 5C. The skin section is illuminated as discussed above but in this case the process is much more effective for hair tissue destruction and sebaceous gland tissue destruction because there is a far greater quantity of carbon particles initially in the duct.

Figure 6:
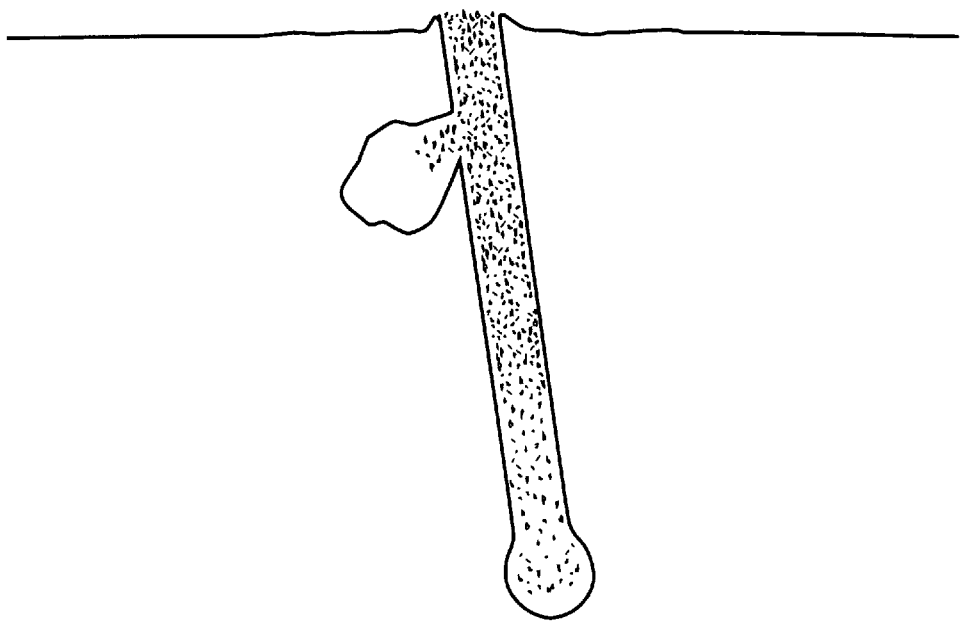
FIG. 6 demonstrates a treatment wherein the hair is removed prior to application of contaminant.

FIG. 6 shows a hair duct in which the complete hair has been completely removed by a method such as plucking or by extraction with hair extraction wax. Here an even greater quantity of carbon particles can be infiltrated into the duct for even more effectiveness. A good method of removing the hair in preparation for the laser treatment is as follows:

Please a thin layer of super glue on a 2 $cm^2$ section of a glass microscope slide. After five seconds place the treated section of the slide on the skin area to be treated. Leave on the skin for 30 seconds. Lift the slide. This will pull out all hairs by the roots. The ducts can then be infiltrated with contaminant as discussed above.

OTHER EMBODIMENTS

Persons skilled in the laser-medicine art will recognize that many other lasers-contaminant combination could be used to practice this invention. The important attributes of the combinations are:

1) The contaminant must be very highly absorptive of energy at the wavelength of the laser beam when using small particles, the particles preferably should be smaller than 10 microns.

2) The laser beam preferably is a pulsed beam with very short pulses (pulse duration of less than 1 microsecond).

3) The contaminant should be capable of being infiltrated into spaces in the upper layers of the skin.

4) The contaminant should explode with sufficient energy upon absorption of the laser energy to produce the desired results.

Applicants have tested acrylic tattoo inks which have been approved by FDA for tattoo use. Black and blue tattoo inks marketed by Spaulding and Rogers appear to work well with a Nd:YAG laser operating at 1 Hz, 1.06 micron with an energy density of about 3 $J/cm^2$. We had less success with other colors.

While the above description contains many specifications, the reader should not construe these as limitations on the scope of the invention, by merely as exemplifications of preferred embodiments thereof. Those skilled in the art will envision many other possible variations are within its scope. Accordingly the reader is requested to determine the scope of the invention by the appended claims and their legal equivalents, and not by the examples which have been given.

We claim:

1. A skin treatment process for alleviating undesirable epidermal skin conditions caused or exacerbated by biological activity of sebaceous glands, comprising the steps of:
    (a) topically applying to a section of skin a contaminant having a high absorption at at least one frequency band of light which penetrates outer layers of human epidermis,
    (b) forcing some of said contaminant to infiltrate into spaces within or adjacent to sebaceous glands in the skin via hair ducts therein, and
    (c) illuminating said section with pulses of said at least one frequency band of light, so as to impart to the contaminant sufficient energy to explode at least a portion of said infiltrated contaminants thereby damaging said sebaceous glands.

2. A process as in claim 1 wherein said contaminant comprises a large number of carbon particles.

3. A process as in claim 2 wherein an ultrasound device is utilized to force the carbon particles to infiltrate into said spaces.

4. The process as in claim 3 wherein the ultrasound device has about 0.2 watts/$cm^2$ of power and a frequency of about 10 Hz.

5. A process as in claim 2 wherein said pulses are pulses from a Nd:YAG laser.

6. A process as in claim 2 wherein said pulses are pulses from a $CO_2$ laser.

7. A process as in claim 1 wherein explosion of said portion of the contaminant defines a forcing explosion which forces another portion of said contaminant to infiltrate into said spaces.

8. A process as in claim 7 wherein a confinement means, transparent to said at least one frequency band of light is placed over said topically applied contaminant to confine said forcing explosion.

9. A process as in claim 8 wherein said confinement means is a glass plate.

10. A process as in claim 8 wherein said confinement means is a plastic plate.

11. A process as in claim 10 wherein said plastic plate is a part of an articulated arm.

12. The process as in claim 8 wherein the contaminant is a liquid.

13. The process as in claim 12 wherein the contaminant is an aqueous solution comprising indocyanine green or black food coloring.

14. The process as in claim 12 wherein the contaminant is water-based.

15. A process as in claim 1 wherein said contaminant comprises graphite particles with a major dimension of less than 10 microns.

16. A process as in claim 15 wherein said graphite particles are mixed with an oil.

17. A process as in claim 16 wherein said oil is baby oil.

18. A process as in claim 16 wherein said graphite particles have a major dimension of about 1 micron.

19. The process as in claim 18 wherein the ratio of the graphite particles to the oil is about 1:4 by weight.

20. A process as in claim 1 comprising the additional step of removing from said ducts a plurality of hairs in said skin section prior to applying said contaminant.

21. A process as in claim 1 comprising the additional step of removing from said ducts substantially all of the hairs in said skin section prior to applying said contaminant.

22. The process as in claim 1 wherein the undesirable skin condition is acne or seborrhea.

23. The process as in claim 1 or 8 wherein said pulses are provided by a laser.

24. The process as in claim 23 wherein said laser is a Nd:YAG laser.

25. The process as in claim 24 wherein said laser has a power of about 3 Joules/$cm^2$.

26. The process as in claim 24 wherein said at least one frequency band of light has a wavelength of about 1.06 $\mu$m.

27. The process as in claim 24 wherein said pulses have a frequency of about 5 Hz.

28. The process of claim 24 wherein the pulses define a pulse duration and the pulse duration is a few nanoseconds.

29. The process as in claim 23 wherein the beam of the laser has a diameter of about 0.5 cm.

30. The process as in claim 29 wherein the beam of the laser is scanned over said skin so that said section of skin receives said pulses at a frequency of about 1 Hz.

31. The process as in claim 1 or 8 whereby production of collagen fibers in the dermal layer of said section of skin is stimulated.

32. The process as in claim 1 wherein the contaminant is a liquid.

* * * * *